United States Patent [19]

Wang

[11] Patent Number: 5,686,493
[45] Date of Patent: Nov. 11, 1997

[54] METHOD FOR PROTECTING AGAINST ENDOTOXIN-INDUCED SHOCK USING ORNITHINE

[75] Inventor: Soo Ray Wang, Taipei, Taiwan

[73] Assignee: National Science Council, Taipei, Taiwan

[21] Appl. No.: 443,532

[22] Filed: May 18, 1995

Related U.S. Application Data

[62] Division of Ser. No. 44,233, Apr. 7, 1993, Pat. No. 5,436,270.

[51] Int. Cl.$^6$ .................................................. A61K 31/195
[52] U.S. Cl. ........................... 514/565; 514/564; 514/561
[58] Field of Search ........................................ 514/565, 564, 514/561

[56] References Cited

U.S. PATENT DOCUMENTS

| | | | |
|---|---|---|---|
| 5,196,195 | 3/1993 | Griffith | 424/94.6 |
| 5,436,270 | 7/1995 | Wang | 514/565 |

FOREIGN PATENT DOCUMENTS 494848  7/1992  European Pat. Off. .

*Primary Examiner*—Jean C. Witz
*Attorney, Agent, or Firm*—W. Wayne Liauh

[57] ABSTRACT

A method for the prophylaxis of shock in a patient induced by endotoxin or bacteremia is disclosed. The method involves administering a therapeutically effective amount of a chemical composition dissolved in a pharmaceutically compatible solvent to the patient. The preferred chemical composition is ornithine or an ornithine-generating chemical.

2 Claims, No Drawings

METHOD FOR PROTECTING AGAINST ENDOTOXIN-INDUCED SHOCK USING ORNITHINE

This is a divisional application of application Ser. No. 08/044,233, filed Apr. 7, 1993, now U.S. Pat. No. 5,436,270.

FIELD OF THE INVENTION

The present invention relates to a method for protecting against endotoxin-induced shock. More particularly, the present invention relates to a method involving administering a pharmaceutically effective amount of a chemical composition into a patient body to effectuate prophylaxis of septic shock induced by endotoxin and/or bacteremia.

BACKGROUND OF THE PRESENT INVENTION

Septic shock is a life-threatening complication of bacterial infection. The reported number of incidences has been increased since the 1930's. Septic shock is presently the most common cause of mortality and morbidity in non-coronary intensive care units in the United States. Recent estimates suggest incidence of 70,000 to 300,000 cases per year in the United States alone. The overall mortality due to gram negative bacteremia is approximately 20%, with the occurrence of septic shock, which occurs in 15% of batteremic patients, mortality is 50-70%.

Bacteremia is typically defined as bacteria in the bloodstream, and is usually determined by a positive blood culture. Sepsis refers to physiological alterations and clinical consequences of the presence of microorganisms or their products in the bloodstream or tissues. When sepsis is associated with hypotension and signs of poor tissue perfusion, it is called septic shock. Septic shock has traditionally been recognized as a consequence ,of infection with gram-negative bacteria, but it may also be caused by gram positive bacteria, fungi, viruses, and protozoa.

The pathogenesis of septic shock is complex and has not been fully understood. One of the complicating factors is that overlapping and sometimes even opposing effects can be present. Diverse microorganisms can generate toxins such that the release of potential mediators would act on vasculature and myocardium. Studies in both animals and humans have shown that endotoxin is the primary factor that precipitates the shock state. Endotoxin is a lipopolysaccharide molecule that is contained in the cell wall of all gram-negative bacteria. It is released from a focus of infection when gram-negative bacteria are phagocytized by either circulating macrophages or cells of the reticuloendothelial systems.

In the past, the conventional approach in treating endotoxin induced shock had been to administer intravenous injections of excess amounts of glucocorticoids, such as methylprednisolone at dosages of about 30 ml per kilogram. However, this method has been considered largely ineffective.

It has long been known that endotoxin will activate the complement cascade, and via the release of components of the complement system many of the effects of sepsis occur. After invading the bloodstream, microorganisms would begin a cascade of events leading to the release of microbial toxins and harmful host mediators that produce sepsis. The early mediators are thought to consist of microorganism-oriented extoxins and endotoxin, and host effectors such as neutrophils and macrophages, which produce cytokines such as tumor necrosis factor (TNF) and interleukin 1 (IL-1). The release of cytokines in low dose is normally a protective response. However, in the presence of endotoxins the massive release of TNF and subsequent activation of immune cells can lead to persistent uncontrolled systemic inflammation resulting in wide tissue injury and metabolic derangement.

Once released, cytokines would trigger a complex array of further host substances, such as prostaglandins, coagulative and fibrinolytic cascades, nitric oxide (NO), endorphins, interferons, platelet-activating factors. Overall, this network of mediators and toxins affect the systemic and pulmonary vasculatures, the myocardium, and the structures of endothelium, producing hypotension and resulting in death. NO is a potent endothelium-derived relaxing factor (EDRF); it may play a major role in the regulation of microcirculation. In the past, In vitro and in vivo studies have suggested that endotoxin-induced loss of vascular responsiveness is due to the activation of NO which is synthesized from L-arginine and can be blocked by NO synthase inhibitors L-arginine analogues, such as N-nitro-L-arginine methyl ester (L-NAME). Several studies have shown that NO has a major effect in cardiovascular performance in endotoxemia. Inhibition of NO synthesis thus has been considered as being a potentially useful method in the treatment of sepsis.

None of the prior an methods can claim a proven record of success. Therefore, other therapies must be considered to improve survival and reduce morbidity. In recent years, immunotherapy and immunoprophylaxis have been advocated. It was shown that human antiserum and monoclonal antibodies could be effective against endotoxins anti TNF reduced death from gram-negative bacterial infection.

Several U.S. patents have discussed the prophylaxis and treatment of endotoxin induced shock. U.S. Pat. No. 4,388,318 ('318 patent) issued to Koyama, et al. disclosed a method of treating endotoxin shock with a pyrimido-pyrimidine derivative. The basis of the '318 patent is that central adrenergic neurons influence peripheral sympathetic nerve activity and thus cardiovascular regulation. The inhibition of alpha adrenergic receptors in vasomotor centers mediates a decrease in blood pressure, heart rate and peripheral sympathetic activity. Since *E. coli* endotoxin may exert its hypotensive effect by activating the central autonomic blood pressure regulatory circuits, the administering of a pyrimido-pyrimidine derivative, which has a central hypertensive effect acting on the medullary cardiovascular regulatory systems, may stimulate central alpha adrenergic receptors leading to inhibition of brain stem sympathetic pathways that participate in the baroreceptor reflex system.

U.S. Pat. No. 4,822,776 ('776 patent) issued to Cerami and Kawakami disclosed an endotoxin-induced mediator substance, which they suggested may be utilized in procedures as a screening agent to test for potentially effective anti-shock agents. In the '776 patent, it was suggested that the mediator substance can be used to produce antibodies to themselves in rabbits, goats, sheep, chickens, or other mammals. These antibodies may be used as a test for the presence of the mediator substance and administered in pharmaceutical corn positions in response to shock produced by viruses, bacteria, protozoa, etc.

U.S. Pat. No. 5,028,627 ('627 patent) discloses a method using arginine derivatives as arginine antagonists for prophylaxis or treatment of systemic hypotension associated with nitric oxide production or endothelial derived relaxing factor. One embodiment of the inhibitor disclosed in the '627 patent is $N^G$-substituted arginine or an $N^G,N^G$-disubstituted arginine which is administered to animal possibly developing or having a systemic hypotension induced by a biological response modifier. The '627 patent followed the commonly accepted belief that arginine is the physiological precursor of nitric oxide synthesis; it, therefore, concluded that substituted or disubstituted arginine antagonists, such as $N^G$-aminoarginine, $N^G$-nitroarginine, $N^G$-methylarginine, $N^G$-ethylarginine, $N^G$-propylarginine, $N^G$-butylarginine, etc., could inhibit the production in the animal or patient of nitrogen oxide from arginine thus obviating the hypotensive effects of nitrogen oxide.

U.S. Pat. No. 5,068,314 discloses an arginine derivative, which functions as a lipopolysaccharide-binding polypeptide, for removing endotoxin. U.S. Pat. No. 5,175,183 discloses lipoxygenase inhibiting compounds, including N-aryl, N-heteroaryl, N-arylalkyl-, N-heteroarylalkyl, N-aryulcyclopropyl and N-heteroaryl-cyclopropyl-N'-hydroxyurea compounds, in treating disease states including endotoxin shock. U.S. Pat. No. 5,171,739 discloses a method for treatment of endotoxin-associated shock and prevention thereof using a BPI protein effective to bind endotoxin. U.S. Pat. No. 5,162,571 discloses phenol derivatives which have therapeutic and prophylactic activities against endotoxin shock.

SUMMARY OF THE PRESENT INVENTION

The primary object of the present invention is to disclose a method for the prevention of endotoxin-induced shock. More particularly, the primary object of the present invention is to disclose a new approach, which involves administering a pharmaceutically effective amount of a chemical composition into a patient body, to provide prophylaxis of septic shock induced by endotoxin and/or bacteremia.

As described hereinabove, traditional approaches in treating and/or preventing septic shocks have mainly involved using glucocorticoids, LPS-antibodies, NO-synthase inhibitors, and arginine derivatives (as arginine antagonists). However, none of these methods has been clinically proven effective. One of the most difficult problems in developing an effective treatment method lies in the fact that the mechanisms causing the endotoxin-induced shocks have not been fully understood, or may have been incorrectly stated.

In this and other laboratories, arginase, an enzyme important for the urea cycle in the liver, was found to demonstrate as a potent immunosuppressive agent in inhibiting lymphocyte proliferation. In addition to its regulatory effect on plasma arginine level, arginase was also found to inhibit DNA and RNA in the protein syntheses. Since septic shock is highly related to cytokines released by lymphocytes, such as IL-1 and TNF-α, arginase was studied in our laboratory to determine its effect on bacteria-induced septic shock. Intravenous injections of arginase were administered laboratory on mice which were subsequently E. coli-inoculated. Test results positively indicated that arginase administration improved the survival rate of mice after E. coli inoculation.

One possible explanation of the positive effect of arginase on preventing bacteria-induced septic shock is that the enzymatic action of arginase may cause a decrease of arginine and reduce the production of nitric oxide and hence reduce the degree of hypotension. Another possible explanation is that the action of arginase causes an increase in ornithine, which, for some reason, protects mice from death of endotoxic shock. To verify the latter hypothesis, ornithine and arginine injections were administered, respectively, into Balb/c mice, prior to the injection of E. coli LPS. Both were found to show specific protective effect from death of endotoxic shock. The injection of arginine as disclosed in the present invention is contrary to the conventional theory, as various arginine antagonists were often disclosed in the prior art in treating endotoxin-induced shock. The administering of ornithine in the prevention against entotoxin-induced shock was never suggested in the prior art. The findings disclosed in the present invention indicate that the nitric oxide pathway disclosed in the prior art in explaining the mechanism of endotoxic shock may play a less significant role than what has been commonly believed.

As a corollary to the arginase-arginine-orithine study, the effect of spermidine was also studied. Ornithine can be converted to putrescine, which can be further converted to two polyamines: spermidine and spermine. Administering of spermidine injection into Balb/c mice also showed, a positive effect in preventing from death of endotoxic shock. The polyamines, spermidine and spermine, are polycations which are widely distributed in animal cells, although they differ in their relative concentrations. They are synthesized inside the cell in a strictly regulated fashion. Both spermidine and spermine, as well as the diamine putrescine, have been shown to have anti-inflammatory properties. However, the exact mechanism of action of polyamines as anti-inflammatory agents is not known.

In managing bacterial infection, prevention of sepsis should be the goal. The need for treatment of sepsis reflects failure of prevention. Treatment of septic shock emphasizes on prompt and aggressive management with cardiopulmonary support including volume resuscitation, use of vesopressors and inotropic agents, and hemodynamic monitoring in the intensive care unit and use of antimicrobial agents.

DETAILED DESCRIPTION OF PREFERRED EMBODIMENTS

The present invention will now be described more specifically with reference to the following examples. It is to be noted that the following descriptions of examples including preferred embodiments of this invention are presented herein for purpose of illustration and description; it is not intended to be exhaustive or to limit the invention to the precise form disclosed.

EXAMPLE 1

E. coli ATCC 25,922 was purchased from American Type Culture Collection, Maryland, U.S.A. Pure cultures were first grown on nutrient agar plates (Difco). Then a single colony of the freshly-prepared pure culture was transferred into a nutrient broth (Difco) and cultured at 37° C. in a water bath with a shaker. The turbidity of the bacteria culture in the nutrient broth was recorded by measuring $OD_{530}$ hourly using a Spectronic-20 until the turbidity of the broth reached a plateau in a complete growth curve. The number of bacteria in the nutrient was determined by homogeneously plating 0.1 ml of serially diluted bacteria onto a nutrient agar plate and incubated at 37 ° C. for 18–24 hours. The agar plates, 9 cm in diameter with colony counts between 30 and 300, were selected for the measurement of bacteria. A masterbatch of E. coli broth was prepared by growing pure cultures in a nutrient broth (Difco, Detroit, Mich.) for 6–7 hours until a concentration of $7 \times 10^8$ colony forming units (CFU) per ml was reached. The turbidity at the wavelength of 650 nm, was measured to be about 0.5. The masterbatch E. coli broth was diluted with PBS (phosphate buffered saline) by a factor of 20 to obtain diluted E. coli suspensions at a concentration of $3.5 \times 10^7$ colony forming units per ml.

The mice used in this study were male Balb/c having a body weight around 25 g. Intraperitoneal injection of the diluted E. coli. suspensions were then administered to the mice. Prior to the injection of the E. coli suspension, PBS solutions containing various arginase dosages and PBS alone, were injected intravenously into the tail vein of the mice to observe the effect of arginase against septic shock. The arginase used in this study was a mouse liver arginase purified by affinity column using the procedure as described by Wang, S. R., et al. in *Characterization of murine liver-derived inhibitory protein*, Scand. J. Immunol. 3:85–90 (1990), the content of which is incorporated herein by reference. The purified arginase was dissolved in PBS (0.01M sodium phosphate, 0.15NaCl, pH 7.4). The arginase thus purified was highly homogeneous as verified using sodium dodecyl sulfate polyacrylamide gel electrophoresis following the procedure described by Wang, S. R., et al., in *Purification of murine liver-derived inhibitory protein (LIP)*, Chinese J. Microbiol Immunol. 21:179–87 (1988). The total amount of PBS injection was 1 ml. Mouse survival rates were observed up to 72 hours. The survival rates in both arginase-treated and non-treated groups of mice were analyzed using the Fisher's exact test. Results of this set of tests were summarized in Table 1. Without arginase, the survival rate was 20%. With arginase injection, the survival rate had increased to 85% for an amount of 15 micrograms of arginase injection per mouse. The survival rate progressively increased with increased dosage of arginase injected. The survival rates at 5/3 and 5 micrograms per gram mouse were 35% and 55%, respectively.

EXAMPLE 2

0.5 mg. of E. coli lipopolysaccharide (LPS) solution dissolved in 2 ml PBS was injected intraperitoneally into Balb/c mice. The E. coli LPS was serotype 0111:B4 obtained from Sigma, St. Louis, Mo. One day prior to the injection of the lipopolysaccharide solution, various dosages of arginine dissolved in 2 ml PBS (final pH at about 7.0) were intraperitoneally injected into the mice to observe the effect of arginine injection against endotoxin-induced shock. Ordinary Balb/c mice could tolerate up to 0.8 m moles of arginine without death. The test results, which are summarized in Table 2, indicate that the rate of survival of mice after the injection of lipopolysaccharide also increased with the dosage of arginine injected. At an arginine injection of 0.5 m mole per mouse, the increment in survival rate reached a statistically significant level.

EXAMPLE 3

The test conditions were identical to those in Example 2, except that the dosage of arginine was fixed at 0.5 m mole per mouse. The results are similar to the last case reported in Example 2. Results listed in Table 3 further confirmed the effect of arginine increased the survival rate of mice at a statistically significant level, after the injection of lipopolysaccharide. Results of test conditions with PBS injection alone were also reported in Table 3 for comparison.

EXAMPLE 4

The test conditions were identical to those in Example 3, except that ornithine instead of arginine was dissolved in 2 ml PBS (final pH at about 7.0) and was intraperitoneally injected into the mice. The dosage of ornithine was fixed at the same level of 0.5 m mole per mouse, as in Example 3. Results listed in Table 3 indicated the injection of ornithine also increased the survival rate of mice, after the injection of lipopolysaccharide, at a statistically significant level.

EXAMPLE 5 (COMPARATIVE STUDY)

The test conditions were identical to those in Example 3, except that 0.5 m mole per mouse of lysine instead of arginine was dissolved in 2 ml PBS (final pH >7.0) and was intraperitoneally injected into the mice. Results listed in Table 3 indicated the injection of lysine did not have any effect on the survival rate of mice after the injection of lipopolysaccharide. Hence, the protective effect of arginine and ornithine is not a generic property of amino acids; rather, it is related to certain specific properties of arginine and ornithine.

EXAMPLE 6 (COMPARATIVE STUDY)

The test conditions were identical to those in Example 3, except that 0.5 m mole per mouse of alanine instead of arginine was dissolved in 2 ml PBS (final pH at about 7.0) and was intraperitoneally injected into the mice. Results listed in Table 3 indicated the injection of alanine did not have any effect on the survival rate of mice after the injection of lipopolysaccharide. Again, this experiment indicates that the protective effects of arginine and ornithine against endotoxin-induced shock are not a general property of amine acids, but are a specific property of arginine and ornithine.

EXAMPLE 7

0.9 mg of E. coli lipopolysaccharide solution dissolved in 2 ml PBS was injected intraperitoneally into Balb/c mice. One day prior to the injection of the lipopolysaccharide solution, 10 mg of spermidine dissolved in 2 ml PBS was intraperitoneally injected into the mice to observe the effect of spermidine injection against endotoxin-induced shock. Results listed in Table 4 indicated the injection of spermidine also increased the survival rate of mice after the injection of lipopolysaccharide at a statistically significant level. Table 4 also contains controlled test results from administering PBS injection only.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are with the scope of the present invention as determined by the appended claims when interpreted in accordance with the breadth to which they are fairly, legally, and equitably entitled.

TABLE 1

| | Arginase Dosage (μg/mouse) | | | |
|---|---|---|---|---|
| Exp. No. | 0 | 5/3 | 5 | 15 |
| 1 | 0/5* | 2/5 | 3/5 | 5/5 |
| 2 | 1/5 | 1/5 | 1/5 | 3/5 |
| 3 | 2/5 | 3/5 | 4/5 | 5/5 |
| 4 | 1/5 | 1/5 | 3/5 | 4/5 |
| total | 4/20 | 7/20 | 11/20 | 17/20 |
| survival rate | 20% | 35% | 55% | 85% |
| p value+ | | >0.1 | =0.05 | <0.001 |

*number of mice survived over mice tested.
+comparing with the control case with no arginase added.

TABLE 2

| Arginine Dosage (m mole/mouse) | 0 | 0.125 | 0.25 | 0.5 |
|---|---|---|---|---|
| survived/total | 6/20 | 5/20 | 10/20 | 16/20 |
| survival rate | 30% | 25% | 50% | 80% |
| p value* |  | NS[+] | NS | <0.01 |

*Comparing with the control case with no arginase added.

[+]Not statistically significant

TABLE 3

|  | Arginine | Ornithine | Lysine | Alanine | PBS |
|---|---|---|---|---|---|
| survived/total | 21/24 | 17/24 | 1/14 | 6/15 | 8/29 |
| survival rate | 87.5% | 70.8% | 7.1% | 40.0% | 27.6% |
| p value* | <0.001 | <0.01 | NS | NS |  |

*Comparing with the control case with PBS only.

TABLE 4

| Experiment No. | With Spermidine | With PBS only |
|---|---|---|
| 1 | 4/5 | 1/5 |
| 2 | 5/6 | 3/7 |
| 3 | 3/3 | 1/3 |
| 4 | 4/6 | 1/2 |
| 5 | 4/5 | 3/8 |
| survived/total | 20/25 (80%) | 9/25 (36%) |
| p value | <0.01 |  |

What is claimed is:

1. A method for the treatment of shock induced by endotoxin or bacteremia comprising administering to a patient in need of said treatment a bolus injection of a therapeutically effective amount of ornithine dissolved in a pharmaceutically acceptable carrier.

2. The method of claim 1 wherein said pharmaceutically acceptable carrier is phosphate buffered saline.

* * * * *